(12) United States Patent
Yamazaki et al.

(10) Patent No.: US 6,919,316 B2
(45) Date of Patent: *Jul. 19, 2005

(54) IMMUNOSUPPRESSIVE AGENT

(75) Inventors: Takayuki Yamazaki, Noda (JP); Fumio Sugawara, Niiza (JP); Keisuke Ohta, Noda (JP); Kengo Sakaguchi, Tsukuba (JP); Noriko Asano, Chiba (JP); Mika Takenouchi, Tokyo (JP); Kazuyoshi Masaki, Sakado (JP); Noriyuki Sato, Sapporo (JP); Tatsuya Fujita, Sapporo (JP); Hiroeki Sahara, Berkeley, CA (US)

(73) Assignee: Toyo Suisan Kaisha, Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/744,652

(22) Filed: Dec. 23, 2003

(65) Prior Publication Data

US 2004/0142881 A1 Jul. 22, 2004

Related U.S. Application Data

(63) Continuation of application No. PCT/JP01/05942, filed on Jul. 9, 2001.

(51) Int. Cl.$^7$ ................................................. C07H 1/00
(52) U.S. Cl. ........................... 514/25; 536/4.1; 536/54; 536/118
(58) Field of Search ............................. 514/25; 536/4.1, 536/54, 118

(56) References Cited

U.S. PATENT DOCUMENTS

| | | | |
|---|---|---|---|
| 5,489,578 A | 2/1996 | Rosen et al. | |
| 5,695,752 A | 12/1997 | Rosen et al. | |
| 5,783,693 A | 7/1998 | Bertozzi et al. | |
| 6,395,886 B1 | 5/2002 | Yamazaki et al. | |
| 6,444,795 B1 | 9/2002 | Yamazaki et al. | |
| 6,518,248 B1 | 2/2003 | Yamazaki et al. | |
| 6,518,410 B2 | 2/2003 | Yamazaki et al. | |
| 6,740,640 B2 * | 5/2004 | Yamazaki et al. | 514/25 |
| 2002/0022597 A1 | 2/2002 | Yamazaki et al. | |
| 2002/0028776 A1 | 3/2002 | Yamazaki et al. | |
| 2002/0028777 A1 | 3/2002 | Yamazaki et al. | |
| 2002/0052327 A1 | 5/2002 | Yamazaki et al. | |
| 2002/0173471 A1 | 11/2002 | Yamazaki et al. | |

FOREIGN PATENT DOCUMENTS

| | | |
|---|---|---|
| JP | 55-130996 | 10/1980 |
| JP | 3-35816 | 3/1991 |
| JP | 3-52815 | 3/1991 |
| JP | 3-66603 | 3/1991 |
| JP | 60-40159 | 9/1991 |
| JP | 3246203 | 11/1991 |
| JP | 7-149786 | 6/1995 |
| JP | 7-242691 | 9/1995 |
| JP | 9-268198 A | 10/1997 |
| JP | 11-106395 | 4/1999 |
| JP | 2000-143516 | 5/2000 |
| WO | WO 91/02521 | 3/1991 |
| WO | WO 97/40838 | 11/1997 |
| WO | WO 0052021 A1 | 9/2000 |
| WO | WO 0053190 A1 | 9/2000 |

OTHER PUBLICATIONS

Shinya Hanashima, et al., "Structure–Activity Relationship of a Novel Group of Mammalian DNA Polymerase Inhibitors, Synthetic Sulfoquinovosylacylglycerols", *Jpn. J. Cancer Res.*, Oct., 2000, vol. 91, pp. 1073 to 1083.

Keisuke Obta et al., "Sulfoquinovosyldiacylglycerol, KMO43, a New Potent Inhibitor of Eukaryctic DNA Polymerases and HIV–Reverse Transcriptase Type 1 from a Marine Red Alga, *Gigartina ternella*", *Chem. Pharm. Bull.*, 46(4), 684–696 (1998).

Hideaki Shirahashi et al., "Isolation and Identification of Anti–tumor–Promoting Principles from the Fresh–Water Cyanobacterium *Phormidium tienue*", *Chem. Pharm. Bull.*, 41(9), 1664–1666 (1993).

H. Sahara et al., "In vivo anti–tumour effect of 3'–sulphono–quinovosyl 1'–monoacylglyceride isolated from sea urchin (*Strongylocentrotus intermedius*) intestine", *British Journal of Cancer*, 75(3), 324–332 (1997).

P.Q. Liem et al., "Structures teneurs et compositions des esters sulfuriques sulfoniques, phosphoriques des glyesyl–diglycerides de trois fucaceas", *Biochimie*, 1976, vol. 58, pp. 1367–1380.

Michael Keusgen et al., "Sulfoquinovosyl Diacylglycerols from the Alga *Heterosigma carterae*", *Lipids*, 1101–1112, 32, (1997).

(Continued)

*Primary Examiner*—Elli Peselev
(74) *Attorney, Agent, or Firm*—Frishauf, Holtz, Goodman & Chick, P.C.

(57) ABSTRACT

An immunosuppressive agent comprising, as an effective ingredient, at least one compound selected from the group consisting of compounds represented by general formula (1) below and pharmaceutically acceptable salts thereof:

(1)

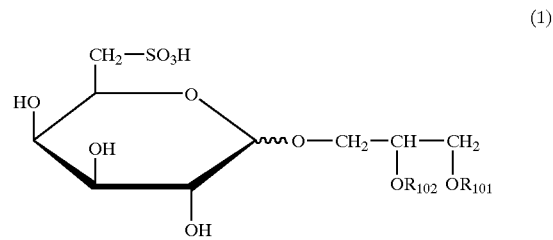

wherein $R_{101}$ represents an acyl residue of a higher fatty acid, and $R_{102}$ represents a hydrogen atom or acyl residue of a higher fatty acid.

18 Claims, 1 Drawing Sheet

OTHER PUBLICATIONS

Roy Gigg et al., "Synthesis of 3—O—(6–Deoxy–6–sulpho–α–D–glucopyranosyl)–1,2–di–O–hexadecanoyl–L–glycerol, Sulphoquinovosyl Dig–lyceride", *Journal of the Chemical Society Perkin Transaction I*, 2490–2493 (1980).

Dan M. Gordon et al., "Synthesis of a Cyanobacterial Sulfolipid: Confirmation if Its Structure, Stereochemistry, and Anti–HIV–1, Activity", *J. Amer. Chem. Soc.*, 114, 659–663 (1992).

Byeng Wha Son, "Glycolipids from *Gracilaria verrucosa*", *Phytochemistry*, 29, 307–309 (1990).

Vishwanath et al., "Interaction of Plant Lipids with 14 kDA Phospholipase $A_2$ Enzymes," *Biochemical Journal*, 320(1), 93–99 (Nov. 15, 1996).

Golik et al., "Isolation and Structure Determination of Sulfonoquinovosyl Dipalmitoyl Glyceride, a P–Selectin Receptor Inhibitor from the Alga *Dictyochloris fragrans*," *Journal of Natural Products*, 60(4), 387–389 (Apr., 1997).

Murakami et al., "Enzymatic Transformation of Glyceroglycolipids into sn–1 and sn–2 Lysoglyceroglycolipids by Use of *Rhizopus arrhizus* Lipase," *Tetrahedron*, 50(7), 1993–2002 (Feb. 14, 1994).

K. Ohta et al, Action of a New Mammalian DNA Polymerase Inhibitor, Sulfoquinovosyldiacylglycerol, *Biological & Pharmaceutical Bulletin*, Feb. 1999, vol. 22, No. 2, pp. 111–116.

Yoshiyuki Mizushina, Shonen Yoshida, Akio Matsukage and Kengo Sakaguchi, "The Inhibiting Action of Fatty Acids on DNA Polymerase β", *Biochimica et Biophysica Acta*, 1336, (1997), 509–521.

Peer et al., "Synthesis of an L–Fucose–Derived Cyclic Nitrone and its Conversion to α–L–Fucosidase Inhibitors," *Helvetica Chemica Acta*, 82(7), 1044–1065 (Jul. 7, 1999).

Sanders et al., "Synthesis of Sulfated Trisaccharide Ligands for the Selectins," *Tetrahedron*, 53(48), 16391–16422 (Dec. 1, 1997).

Arasappan et al., "Regiospecific 4, 6–Functionalization of Pyranosides via Dimethylboron Bromide–Mediated Cleavage of Phthalide Orthoesters," *J.American Chemical Society*, 117(1), 177–183 (Jan. 11, 1995).

Thiem et al., "Synthesen von Methyl–4–O–(β–D–curaocsyl)–α–D–curamicosid, dem Glycosid der Disaccharideinheit E–F von Flambamycin und Isomeren," *Justus Liebig's Annalen der Chemie*, 1987(4), 289–295 (Apr., 1987).

Fujimaki et al., "Conversion of 1, 6–Anhydromaltose into Pseudodisaccharides Containing Aminocyclitols as Constituent," *Agricultural & Biological Chemistry*, 44(9), 2055–2059 (Sep. 1980).

Akio Ogawa et al., Sulfated Glycoglycerolipid from Archaebacterium Inhibits Eukaryotic DNA Polymerase α, β and Retroviral Reverse Transcriptase and Affects Methyl Methanesulfonate Cytotoxicity, *International Journal of Cancer*, 76, 512–518 (1998).

Gerhard Kretzschmar et al., "Short Synthesis of Sulfatide– and SQDG–Mimetics as Small Molecular Weight Selectin Inhibitors", *Tetrahedron*, 54, 15189–15198 (1998).

Bernd Meyer et al., Syntheses of Benzyl 6–O–Sulfo–β–D–glucopyranoside Salts and Their 6S–Deuterated Analogues. Conformational Preferences of Their (Sulfonylaxy)methyl Group, *Journal of Organic Chemistry*, 55, 902–906 (1990).

Kitagawa et al., "Sulfonoglycolipid from the Sea Urchin *Anthocidaris crassispina A. Agassiz*," *Chemical and Pharmaceutical Bulletin*, 27(8), 1934–1937 (Aug. 1979).

Rastrelli, Luca, "Glycolipids from *Byrsonima crassifolia*," *Phytochemistry*, 45, 647–650 (1997).

Yoshiyuki Mizushina, Sinya Hanashima, Kengo Sakaguchi, Fumio Sugawara and Keisuke Ohta, "Search and Structural Identification of Inhibitory Substance on DNA Polymerase of Higher Organisms", published by Kokki Sakai, Kyusho University, Fukuoka City, Japan, "A Collection of Summaries of Lectures at Convention of Natural Organic Compounds", Aug. 31, 1998, $40^{th}$ lecture, pp. 493–498.

Hideo Nakane and Kasuhiko Ono, "Inhibitor of DNA Polymerase Activity", *Metabolism*, vol. 28, No. 12, pp. 1027–1034 (1991).

Tulloch et al., "Combination and Positional Distribution of Fatty Acids in Plant Sulfolipids." *Hoppe–Seyler's Zeitschrift Physiol. Chem.*, 354. 879–889 (Aug. 1973).

Fusetani et al., "Structures of Two Water Soluble Hemolysins Isolated from the Green Alga *Ulva pertusa*," *Agricultural and Biological Chemistry*, 39(10), 2021–2025 (Oct. 1975).

Gustafson et al., "AIDS–Antiviral Sulfolipids From Cyanobacteria (Blue–Green Algae)," *Journal of the National Cancer Institute(USA)*, 81(16), 1255–1258 (Aug. 16, 1989).

Adebodun et al., "Spectroscopic Studies of Lipids and Biological Membranes: Carbon–13 and Proton Magic–Angle Sample–Spinning Nuclear Magnetic Resonance Study of Glycolipid–Water Systems," *Biochemistry*, 31(18), 4502–4509 (May, 1992).

Gage et al., "Comparison of Sulfoquinovosyl Diacylglycerol from Spinach and the Purple Bacterium *Rhodobacter sphaeroides* by Fast Atom Bombardment Tandem Mass Spectrometry," *Lipids*, 27(8), 632–636 (Aug., 1992).

Morimoto et al., "Studies on Glycolipids. VII. Isolation of Two New Sulfoquinovosyl Diacylglycerols from the Green Alga *Chlorella vulgaris*," *Chemical & Pharmaceutical Bulletin*, 41(9), 1545–1548 (Sep. 1993).

Amarquaye et al., "A New Glycolipid from *Byrsonima crassifolia*," *Planta Medica*, 60(1), 85–86 (Feb., 1994).

Golik et al., "Isolation and Structure Determination of Sulfonoquinovosyl Dipalmitoyl Glyceride, a P–Selectin Receptor Inhibitor from the Alga *Dictyochloris fragrans*," *Journal of Natural Products*, 60(4), 387–389 (Apr. 1997).

Vasänge et al., "A Sulfonoglycolipids from the Fern *Polypodium decumanum* and its Effect on the Platelet Activating–factor Receptor in Human Neutrophils," *Journal of Pharmaceutical Pharmacology*, 49(5), 562–566 (May, 1997).

Kim et al., "Structural Identification of Glycerolipid Molecular Species Isolated from Cyanobacterium *Synechocytis* sp. PCC 6803 Using Fast Atom Bombardment Tandem Mass Spectrometry," *Analytical Biochemistry*, 267, 260–270 (1999).

S. Kashima et al., "A Study of Polymerase Inhibitors of Higher Plants, Nippon Nogeikagaku Kaishi", vol. 72, Mar. 5, 1998, p. 82, Abstr. No. 2A12P22.

Yoshiyuki Mizushina et al., "Studies on Inhibitors of Mammalian DNA Polymerase α and β", *Biochemical Pharmacology*, 55, 537–541 (1998).

* cited by examiner

IMMUNOSUPPRESSIVE AGENT

CROSS-REFERENCE TO RELATED APPLICATIONS

This is a Continuation Application of PCT Application No. PCT/JP01/05942, filed Jul. 9, 2001, which was not published under PCT Article 21 (2) in English.

BACKGROUND OF THE INVENTION

1. Field of the Invention

The present invention relates to a novel immunosuppressive agent. Specifically, the present invention relates to an immunosuppressive agent containing, as an effective ingredient, a sulfofucosylacylglycerol derivative. More specifically, the present invention relates to an immunosuppressive agent containing, as an effective ingredient, sulfofucosylmonoacylglycerol, i.e., 3-0-(6-deoxy-6-sulfo-α/β-D-galactopyranosyl)-1-0-acylglycerol and/or sulfofucosyldiacylglycerol, i.e., 3-0-(6-deoxy-6-sulfo-α/β-D-galactopyranosyl)-1,2-0-diacylglycerol}.

2. Description of the Related Art

In clinical treatment presently performed, transplantation can be employed to treat chemotherapeutically untreatable diseases. Transplantation is the technology for treating a disease by replacing partly or entirely of a diseased organ with a healthy organ taken from another individual. Organ transplantation has been performed with respect to a wide variety of organs such as kidney, liver, lung, intestine, heart, pancreas, and cornea. The number of organ transplantations has been increased.

The immune response of skin is inherently high. However, skin transplantation can be made successfully if a graft skin transplanted from one person to another can be kept alive for at least a few weeks. This is because new dermal tissue, if a graft epidermis is kept alive for a few weeks, can regenerate itself, thereby recovering from a dermal tissue damage. Therefore, it is possible to make physical recuperation of serious and extensive burn or laceration by transplanting a dermal tissue from another person.

The most fearful problem residing in tissue or organ transplantation is a rejection caused by a recipient's immune response.

Under these circumstances, in order to develop an immunosuppressive agent capable of preventing the rejection in a recipient, thereby attaining permanent fixation of a transplanted organ, intensive studies have been conducted since the 1970s, particularly in European countries and U.S.A.

On the other hand, an immunosuppressive agent may also be important in treating autoimmune diseases such as rheumatism and collagen disease, since it can mitigate the symptoms to a certain degree.

Up to the present, cyclosporin A and FK506, etc., have been developed as immunosuppressive agents. However, the functional mechanisms of these immunosuppressive agents resemble each other and their chronic toxicity is a matter of concern. Thus, to attain prolonged life in next-generation organ transplantation, another type of immunosuppressive agent is desired which has a lower toxicity based on a different chemical structure, and thus, different functional mechanism can be expected.

It has been found that naturally-occurring sulfur-containing glycolipids have pharmaceutical activities such as an anticancer effect (Sahara et al., British Journal of Cancer, 75(3), 324–332, (1997)); inhibitory activities against DNA polymerase (Mizushina et al., Biochemical Pharmacology, 55, 537–541 (1998), Ohta et al., Chemical & Pharmaceutical Bulletin, 46(4), (1998)); and HIV suppressive effect (National Patent Publication No. 5-501105). However, it has not yet been found that a sulfur-containing glycolipid, in particular, a sulfofucosylacylglycerol derivative, has an immunosuppressive activity.

BRIEF SUMMARY OF THE INVENTION

An object of the present invention is to provide a novel immunosuppressive agent. More specifically, the object of the present invention is to provide an immunosuppressive agent showing low toxicity and usability of long-term administration, and high immunosuppressive activity as well.

The present inventors have conducted studies to attain the aforementioned object. As a result, they found that specific sulfofucosylacylglycerol derivatives have a remarkable immunosuppressive activity and accomplished the present invention. The present invention provides an immunosuppressive agent containing, as an active ingredient, at least one compound selected from the group consisting of:

compounds represented by Formula (1):

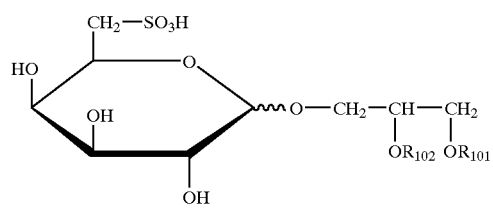

(1)

wherein $R_{101}$ represents an acyl residue of a higher fatty acid, and $R_{102}$ represents a hydrogen atom or acyl residue of a higher fatty acid; and a pharmaceutically acceptable salt thereof.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

DETAILED DESCRIPTION OF THE INVENTION

Figure 1:
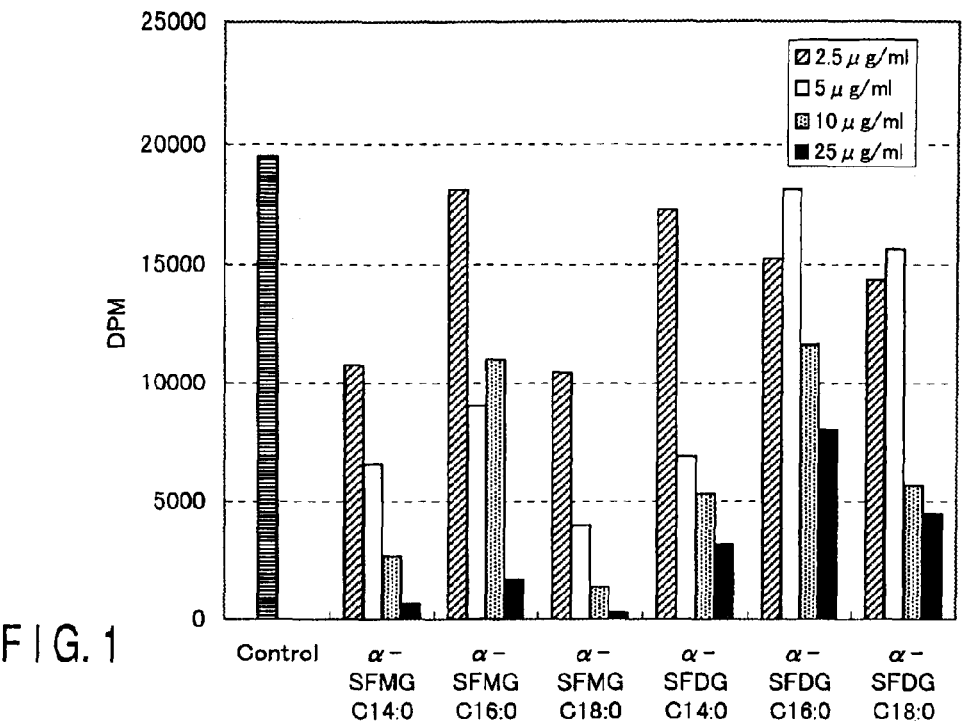
FIG. 1 is a graph showing immunosuppressive activity of the compound represented by the general formula (1) of the present invention.

In the specification, the term "carbon atoms" of a protecting group refers to the number of carbon atoms assuming that the protecting group is unsubstituted. To be more specific, when the group represented by $R^1$ is a substituted alkyl group, its number of carbon atoms is that of the alkyl group itself, and the number of carbon atoms of the substituent on the alkyl group is not counted. The same conditions are applicable to the case where the protecting group is other than the alkyl group.

In the first place, we will more specifically explain the active ingredient contained in the immunosuppressive agent of the present invention, that is, a sulfofucosylacylglycerol derivative represented by Formula (1):

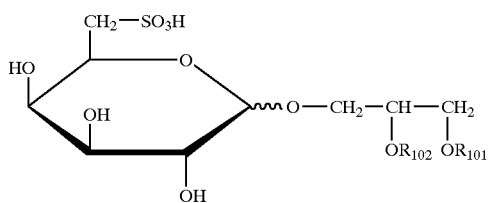

(1)

wherein $R_{101}$ represents an acyl residue of a higher fatty acid, and $R_{102}$ represents a hydrogen atom or acyl residue of a higher fatty acid.

In the general formula (1), fatty acids giving the acyl residues represented by $R_{101}$ include straight-chain or branched-chain, saturated or unsaturated higher fatty acids. More specifically, the acyl residues of straight-chain or branched-chain higher fatty acids represented by $R_{101}$ include groups represented by R—C(=O), where R represents an alkyl or alkenyl group having 13 or more carbon atoms. The number of carbon atoms of the alkyl and alkenyl groups represented by R of R—C(=O) is preferably 13 or more and 25 or less, and more preferably, an odd number within 13–25, in view of the immunosuppressive activity, the production costs and etc. The preferable numbers of carbon atom of R mentioned above, i.e., 13 or more and 25 or less, correspond to 14 or more and 26 in terms of the number of the carbon atoms of acyl residues. Also, the more preferable number of carbon atoms of R mentioned above, i.e., odd numbers within 13–25, correspond to even numbers of 14–26 in terms of the number of the carbon atoms of acyl residues.

In the general formula (1), $R_{102}$ represents a hydrogen atom of acyl residue of a higher fatty acid. The acyl residue represented by $R_{102}$ has the same meaning as $R_{101}$ mentioned above. $R_{102}$ is preferably a hydrogen atom judging from the results of immunosuppressive activity assay using cultured cells.

When both $R_{101}$ and $R_{102}$ are acyl residues of a higher fatty acid(s), $R_{101}$ and $R_{102}$ may be the same or different. However, they are preferably the same in view of manufacturing facility.

The sugar skeleton of fucosyl moiety in Formula (1) may take either a boat or chair conformation. However, the chair conformation is preferable in view of stability. The absolute configuration of the carbon (asymmetric carbon) at the 2-position of the glycerol moiety may be either the S- or R-configuration. The stereoisomer formed by the bonding between fucosyl moiety and glycerol moiety is either an α-anomer or β-anomer.

The sulfofucosylacylglycerol derivatives represented by the general formula (1) of the invention may be synthesized by referring to the methods described in PCT application No. WO 00/52021 filed by the assignee of the present application.

Further, by carrying out the processes (Step A to Step K) shown in the following scheme 1, the β-anomer of the general formula (1) may be selectively prepared.

Scheme 1

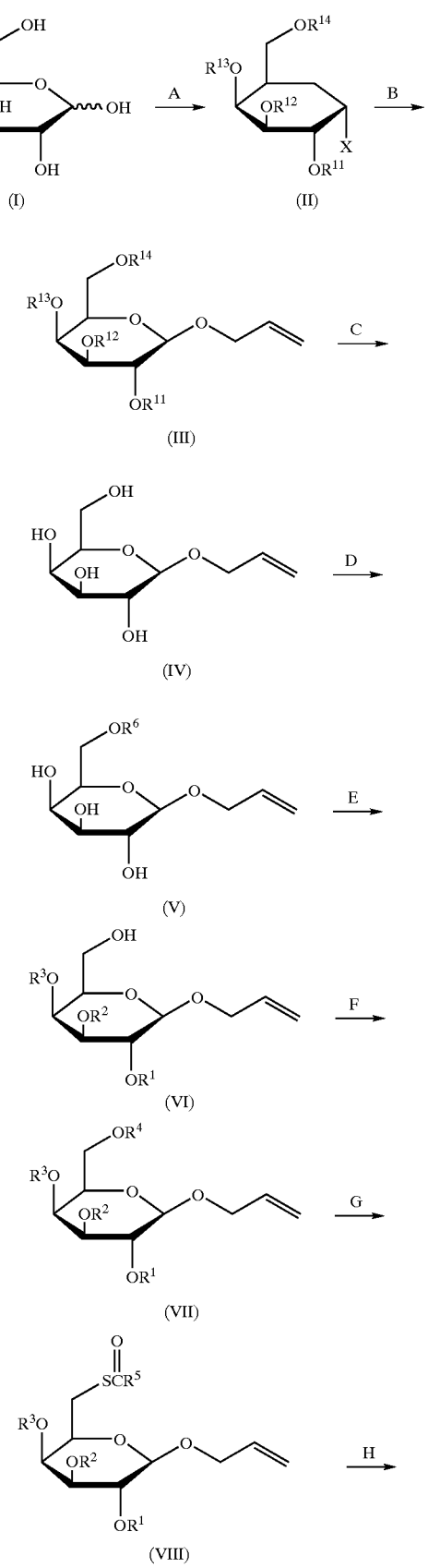

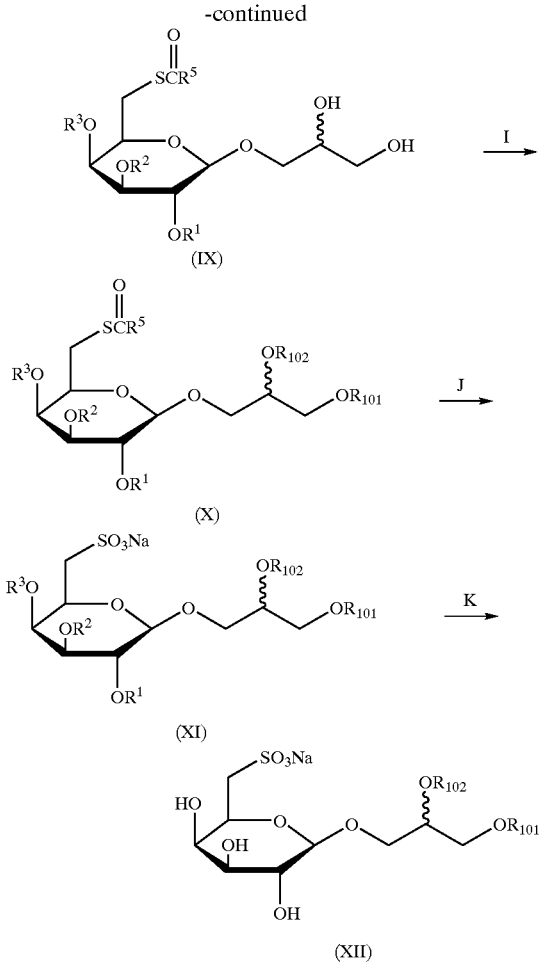

(Step A) Hydroxyl groups bonded to the C1 to C4 and C6 carbons of galactose are protected with acyl-based protective groups. Thereafter, the C1 carbon is substituted with a halogen, such as bromine, whereby a galactose derivative (α-anomer) is obtained. (Step B) The halogen bonded to the C1 carbon of the galactosyl moiety is substituted with 2-propenyl group, whereby, via neighboring group participation, a galactose derivative (β-anomer) is selectively obtained. (Step C) The protective groups at the C2 to C4 and C6 carbons of the galactosyl moiety are deprotected. (Step D) The hydroxyl group bonded to the C6 carbon of the galactosyl moiety is protected. (Step E) The hydroxyl groups bonded to the C2, C3 and C4 carbons of the galactosyl moiety are protected. Thereafter, the protective group at the C6 carbon is deprotected. (Step F) The hydroxyl group bonded to the C6 carbon of the galactosyl moiety is substituted with a group which can be converted to carbonylthio group (e.g., alkylsulfonyloxy group or arylsulfonyloxy group). (Step G) The C6 carbon is converted into a carbonylthio group. (Step H) The 2-propenyl group bonded to the C1 carbon of the galactosyl moiety is converted into a dihydroxylated product. (Step I) The obtained dihydroxylated product is subjected to esterification by using a desired higher fatty acid. (Step J) The carbonylthio group at the C6 carbon of the galactosyl moiety is converted into a sulfonate salt. (Step K) The protective groups of the C2, C3 and C4 carbons of thus obtained sulfonate salt are deprotected, whereby a sulfofucosylacylglycerol derivative, which is in the form of a salt, is prepared. The salt thus obtained is subjected to titration with an acid, such as hydrochloric acid, to give the sulfofucosylacylglycerol derivative represented by the general formula (1).

The aforementioned Steps A to J will be described further in detail hereafter.

The protection of the hydroxyl groups bonded to the C1 to C4 and C6 carbons of galactose in Step A can be carried out by esterifying the hydroxyl groups with an acid, such as acetic anhydride, in the presence of a catalyst, such as perchloric acid. In general, this esterification reaction can be carried out at a temperature in the range of 30 to 40° C. for thirty minutes to three hours. However, the reaction time may vary depending on the reaction conditions.

Next, a halogen, such as bromine, is reacted with the protected galactose, so that the halogen atom, such as bromine, is bonded to the C1 carbon of the galactose. This halogenation reaction can be carried out by reacting the galactose whose hydroxyl groups have been protected, with the halogen, such as bromine, in the presence of a catalyst, such as red phosphorus. In general, this reaction can be carried out at a temperature not higher than 20° C. for two to five hours. However, the reaction time may vary depending on the reaction conditions.

The substitution of the halogen bonded to the C1 carbon of the galactosyl moiety with 2-propenyl group in Step B can be carried out by dissolving the compound of formula (II) obtained in Step A in a solvent, such as dichloromethane, and reacting the dissolved compound with allyl alcohol in the presence of a catalyst, such as mercury cyanide, generally at a temperature in the range of 0 to 40° C. for a half day to two days. However, the reaction time may vary depending on the reaction conditions.

As a result of this reaction, β-anomer, of the stereoisomers due to the C1 carbon of the galactosyl moiety, is obtained. The steric arrangement of the β-anomer is maintained throughout the subsequent reactions, whereby the desired galactosyl derivative (β-anomer) can be produced.

In Step C, the protective groups at the C2 to C4 and C6 carbons of the galactosyl moiety of the compound of formula (III) can be deprotected by reacting in the presence of an alkali such as sodium methoxide, in a solvent such as methanol, at room temperature for a half day to one day. However, the reaction time may vary depending on the reaction conditions.

In Step D, the hydroxyl group bonded to the C6 carbon of the compound of formula (IV) is protected, whereby a compound of formula (V), in which —OR$^6$ (wherein R$^6$ represents an alkyl group or a substituted silyl group) has been bonded to the C6 carbon, is obtained.

When the group represented by R$^6$ is an alkyl group, the alkyl group is preferably a lower alkyl group having a bulky substituent. Examples of the substituent include methyl group, phenyl group and the like. Specific examples of the substituted alkyl group include t-butyl group, trityl group and the like.

When the group represented by R$^6$ is a substituted silyl group, examples of the substituent of the substituted silyl group include a lower alkyl group which is preferably an alkyl group whose number of carbon atoms is 1 to 4 (e.g., methyl group, ethyl group, isopropyl group, t-butyl group) and an aryl group which is preferably an aryl group whose number of carbon atoms is 6 (e.g., phenyl group). The substituted silyl group represented by R$^6$ is preferably a silyl group having three substituents, such as t-butyldiphenylsilyl group.

When a compound of formula (V), in which R$^6$ is an alkyl group, is to be obtained in Step D, such a compound can be obtained by adding a compound represented by R$^6$—X (wherein $R^6$ represents an alkyl group defined as $R^6$ in the aforementioned formula (V), and X represents a halogen atom, such as a chlorine atom) to a solution of the compound of formula (IV) dissolved in an organic solvent, such as dry pyridine, and reacting them at room temperature in the presence of a catalyst, such as p-dimethylaminopyridine (DMAP). Trityl chloride is preferable as the compound $R^6$—X, in terms of reducing production cost and facilitating the reaction.

On the other hand, when a compound of formula (V), in which $R^6$ is a substituted silyl group, is to be obtained in Step D, such a compound can be obtained by reacting the compound of formula (IV) with t-butyldiphenylsilyl chloride as the compound $R^6$—X, in the presence of a catalyst, such as imidazole, at room temperature for half a day to two days. Note that the reaction time may vary depending on the reaction conditions.

In Step E, the hydroxyl groups bonded to the C2, C3 and C4 carbons of the compound (V) are protected and then the protective group (—$OR^6$) at the C6 carbon is deprotected, whereby a compound of formula (VI) having —$OR^1$, —$OR^2$ and —$OR^3$ bonded thereto is obtained (wherein each of $R^1$ to $R^3$ independently represents an alkyl group or a substituted silyl group).

The protection of the hydroxyl groups bonded to the C2, C3 and C4 carbons of the compound of formula (V) can be carried out, by activating the hydroxyl groups bonded to the C2, C3 and C4 carbons using sodium hydride and the like, and thereby reacting with a compound capable of protecting the hydroxyl groups in an organic solvent such as N,N-dimethylformamide (DMF), at room temperature.

Examples of the compound capable of protecting the hydroxyl group include benzyl bromide, p-methoxybenzyl bromide, t-butyldimethylsilyl chloride, triethylsilyl chloride and the like.

The conditions during the reaction with the compounds capable of protecting the hydroxyl group may be those suitable for the respective protective groups.

When $R^6$ is trityl group, the protective group at the C6 carbon can be deprotected in the presence of an acid catalyst, such as p-toluenesulfonic acid. When $R^6$ is silyl group, the protective group at the C6 carbon can be deprotected in the presence of an acid catalyst, or a fluoride such as tetrabutylammonium fluoride.

In Step F, the hydroxyl group bonded to the C6 carbon of the compound of formula (VI) is converted to —$OR^4$ (wherein $R^4$ represents alkylsulfonyl group or arylsulfonyl group), whereby a compound of formula (VII) is obtained.

The reaction of converting to —$OR^4$ can be carried out by adding a compound having arylsulfonyl group or a compound having alkylsulfonyl group to the solution of the compound of formula (VI) dissolved in an organic solvent, and reacting them.

The aryl group of the compound having the arylsulfonyl group is an unsubstituted or substituted aryl group, which is preferably an aryl group having six carbon atoms (e.g., phenyl group). In the case of the substituted aryl group, examples of the substituent include p-methyl group, p-methoxy group and the like. As the compound having arylsulfonyl group, a compound represented by a formula $R^{4'}$—X (wherein $R^{4'}$ represents arylsulfonyl group and X represents a halogen atom) may be used. Specific examples thereof include p-toluenesulfonyl chloride, p-methoxybenzenesulfonyl chloride and benzenesulfonyl chloride.

On the other hand, the alkyl group of the compound having alkylsulfonyl group is preferably an unsubstituted alkyl group or a substituted alkyl group (e.g., trifluoromethyl group), and more preferably a lower alkyl group, and further more preferably an alkyl group whose number of carbon is 1 to 2 (i.e., methyl group, ethyl group). As the compound having alkylsulfonyl group, a compound represented by a formula $R^{4''}$-L (wherein $R^{4''}$ represents alkylsulfonyl group, and L represents a leaving group) may be used. Specific examples thereof include trifluoromethanesulfonic anhydride, methanesulfonyl chloride and ethanesulfonyl chloride.

Of the above mentioned compounds having alkylsulfonyl group or arylsulfonyl group, those having tosyl group (p-toluenesulfonyl group) are preferable from the viewpoint of reaction facility.

In the reaction of Step F, as an organic solvent, for example, pyridine or dichloromethane may be used.

The reaction mentioned above may be performed, as the case may be, in the presence of a catalyst, such as DMAP, at room temperature for two hours to one day. The reaction time may vary depending on the reaction conditions.

In Step G, the sulfonyloxy group (—$OR^4$) of the compound of formula (VII) is replaced with a carbonylthio group, —SC(=O)$R^5$, wherein $R^5$ represents a hydrogen atom, alkyl group or aryl group.

Specifically, a compound capable of substituting the alkylsulfonyloxy group or the arylsulfonyloxy group of the compound of the formula (VII) with a carbonylthio group, is allowed to react with the compound of formula (VII) dissolved in an organic solvent to give the compound of formula (VIII). Hereinafter this compound will be referred to as "O-substituted→S-substituted compound"

Examples of the "O-substituted→S-substituted compound" include an alkali metal salt and an alkaline earth metal salt of thiocarboxylic acid. Examples of thiocarboxylic acid include thioformic acid, lower thiocarboxylic acids, preferably, an aliphatic thiocarboxylic acid each having 1 to 5 carbon atoms in its aliphatic hydrocarbon moiety (e.g., thioacetic acid, and thiopropionic acid), and aromatic thiocarboxylic acids each having 6 to 10 carbon atoms in its aromatic hydrocarbon moiety (e.g., thiobenzoic acid).

Examples of the alkali metal that forms salt with thiocarboxylic acid include cesium, potassium and sodium. Examples of the alkaline earth metal include magnesium and calcium.

Of the above mentioned "O-substituted→S-substituted compounds", salts of thioacetic acid can be preferably used since a reaction can proceed stably and the sulfur atom can easily oxidized in a later step.

Examples of the organic solvent used in the reaction in Step G include N,N-dimethylformamide, alcohol (preferably a lower alcohol, e.g., methanol, ethanol, propanol), dimethyl sulfoxide and the like.

The aforementioned reaction may be performed usually at room temperature to the boiling point of a solvent to be used while stirring one hour to one day. Note that the reaction time may vary depending on the reaction conditions.

The dihydroxylation in Step H can be performed by adding an oxidizing agent, such as osmium tetraoxide, to the solution of the compound (VIII) dissolved in a solvent mixture, such as a mixture of t-butanol and water, and then reacting the resultant mixture in the presence of a re-oxidizing agent, such as trimethylamine N-oxide, at room temperature for one to three days. The reaction time may vary depending on the reaction conditions.

In Step I, the hydroxyl groups at the glyceridyl moiety of the compound of formula (IX) is subjected to esterification.

This reaction can be carried out by adding a higher fatty acid corresponding to the final product to the solution of the compound (IX) dissolved in a suitable organic solvent, such as dichloromethane, and reacting the resultant mixture, if necessary, in the presence of a suitable esterification agent, such as ethyldimethylaminopropylcarbodiimide (EDCI)-DMAP-based esterification agent and the like.

In the reaction of Step I, as the fatty acid to be added, a higher fatty acid having acyl residue represented by $R_{101}$ of the aforementioned general formula (1), i.e., a saturated or unsaturated higher fatty acid which may be either normal or branched can be used.

As a result of the reaction in Step I, a mixture of diester (β-anomer) and monoester (β-anomer) represented by the general formula (1) of the present invention is obtained. The diester is one in which $R_{101}$ and $R_{102}$ of the compound of formula (X) are both acyl residues of the added higher fatty acid, while the monoester is one in which the acyl residue is bonded only to $R_{101}$, and $R_{102}$ is a hydrogen atom. In the reaction of Step I, two or more types of higher fatty acid may optionally be used as the fatty acids to be added. In this case, diester (β-anomer) represented by the general formula (1), in which $R_{101}$ and $R_{102}$ are of the same type of acyl residue or of acyl residues of different types, and monoesters (β-anomer) represented by the general formula (1), in which the type of acyl residue of $R_{101}$ is different for each monoester, are obtained in a mixed manner.

If necessary, the mixture of the monoester and diester can be isolated from each other by, for example, chromatography, for use in the reactions in the subsequent step, i.e., Steps J and K. Further, production of the monoester is suppressed as much as possible by setting the addition amount of the fatty acid to 2–3 times larger than that of the compound of formula (IX), in terms of mole, thereby the diester can be preferentially obtained.

The conversion into a sulfonate salt in Step J can be carried out by adding an oxidizing agent such as OXONE ($2KHSO_5$, $KHSO_4$, $K_2SO_4$) to the solution of the compound of formula (X) dissolved in an organic solvent, which is buffered with acetic acid and potassium acetate, and then allowing the resultant mixture to react at room temperature for 12 hours to two days. Note that the reaction time may vary depending on the reaction conditions.

The protective groups bonded to the C2 to C4 carbons of the compound of formula (XI) are deprotected in Step K, whereby the desired salt of sulfofucosylacylglycerol is obtained. The deprotection may be carried out by a method suitable for a protective group used and acyl residue of the bonded higher fatty acid. For example, when the protecting group is a benzyl group and each of $R_{101}$ and $R_{102}$ is an acyl residue of a saturated higher fatty acid, the deprotection can be carried out by reacting a solution of the compound of formula (XI) dissolved in an organic solvent, such as ethanol, in the presence of a catalyst such as palladium-activated carbon (Pd—C), under a hydrogen gas atmosphere at room temperature. Further, when at least one of the acyl residues of the higher fatty acid represented by $R_{101}$ and $R_{102}$ is the acyl residue of an unsaturated higher fatty acid, a deprotection method suitable for a protecting group used and capable of retaining the double bond of the unsaturated fatty acid may be employed. For example, when the protecting group is a silyl-based group, the deprotection can be conducted by use of an acid catalyst (e.g., trifluoroacetic acid).

The immunosuppressive agent of the present invention contains, as an active ingredient, at least one compound selected from sulfofucosylacylglycerol derivatives represented by the general formula (1) and pharmaceutical salts thereof. As described above, the sulfofucosylacylglycerol derivatives represented by the general formula (1) include conformational isomers due to the galactosyl moiety, isomers due to the C2 carbon (asymmetric carbon) of the glyceridyl moiety, and stereoisomers due to the steric configuration (α/β) between the glyceridyl moiety and the galactosyl moiety. The immunosuppressive agent of the present invention may contain either only one type of these isomers or two or more types of these isomers in a mixed state, unless the isomers has an adverse effect. Further, the immunosuppressive agent of the present invention can be used together with another compound having immunosuppressive activity of other type(s) and/or a compound having a pharmaceutical activity other than immunosuppressive activity, to obtain a pharmaceutical formulation, unless these compounds have an adverse effect on the immunosuppressive activity.

Examples of the pharmaceutically acceptable salts employed in the immunosuppressive agent of the present invention include, but not limited to, a salt of a monovalent cation such as a sodium or potassium ion.

Hereinafter, the compounds of the group consisting of sulfofucosylacylglycerol derivatives represented by the general formula (1) and pharmaceutically acceptable salts thereof are also referred to as "immunosuppressive substance of the present invention".

The immunosuppressive substance of the present invention can be orally or parenterally administered. Immunosuppressive substance of the present invention can be combined with, for example, a pharmaceutically acceptable excipient or diluent depending on an administration route thereby to form a medicinal formulation.

The forms of the agent suitable for oral administration include, solid-, semi-solid, liquid- and gas-states. Specific examples include, but not limited to, tablet, capsule, powder, granule, solution, suspension, syrup and elixir agents. However, the forms of the agent are not limited to these.

In order to formulate the immunosuppressive substance of the present invention into tablets, capsules, powders, granules, solutions or suspensions, the substance is mixed with a binder, a disintegrating agent and/or a lubricant, and, if necessary, the resultant is mixed with a diluent, a buffer, a wetting agent, a preservative and/or a flavor, by a known method. Examples of the binder include crystalline cellulose, cellulose derivatives, cornstarch and gelatin. Examples of the disintegrating agent include cornstarch, potato starch and sodium carboxymethylcellulose. Examples of the lubricant include talc and magnesium stearate. Furthermore, additives such as lactose and mannitol may also be used as long as they are used conventionally.

Moreover, the immunosuppressive substance of the present invention may be administered in the form of aerosol or inhalant, which is prepared by charging the active substance of liquid- or fine powder-form, together with a gaseous or liquid spraying agent, and, if necessary, a known auxiliary agent such as a wetting agent, into a non-pressurized container such as an aerosol container or a nebulizer. As the spraying agent, a pressurized gas, for example, dichlorofluoromethane, propane or nitrogen may be used.

For parenteral administration, the immunosuppressive substance of the present invention can be administered by injection, percutaneously, rectally or intraocularly.

For the administration by injection, the immunosuppressive substance of the present invention can be injected, for example, hypodermically, intracutaneously, intravenously or intramuscularly. An injection preparation may be formulated by dissolving, suspending or emulsifying the immunosuppressive substance of the present invention into an aqueous or non-aqueous solvent such as a vegetable oil, a synthetic glyceride with a fatty acid, an ester of a higher fatty acid or propylene glycol by a known method. If desired, a conventional additive such as a solubilizing agent, an osmoregulating agent, an emulsifier, a stabilizer or a preservative, may be added to the preparation.

For formulating the immunosuppressive substance of the present invention into solutions, suspensions, syrups or elixirs, a pharmaceutically acceptable solvent such as sterilized water for injection or a normalized physiological saline solution may be used.

For the percutaneous administration, the immunosuppressive substance of the present invention may be administered in the form of ointment, emulsifications, pastae, plasters, liniments, lotions, suspensions in accordance with the state of skin to be treated.

The ointments can be formulated by a known method by kneading the immunosuppressive substance of the present invention with a hydrophobic base, such as Vaseline or paraffin, or a hydrophilic base, such as hydrophilic Vaseline or macrogol. The emulsifying agents and other percutaneous agents may be formulated by a method conventionally used.

For the rectal administration, a suppository can be used. The suppository may be prepared by mixing the immunosuppressive substance of the present invention with an excipient that can be melted at body temperature but is solid at room temperature, such as cacao butter, carbon wax or polyethylene glycol, and molding the resultant material, by a known method.

For the intraocular administration, ophthalmic formulations such as eye drops and eye ointments may be administered. The eye drops are formulated by dissolving or suspending the immunosuppressive substance of the present invention in an aqueous solvent, such as sterilized water, and, if necessary, adding a preservative, buffer, and surfactant.

The immunosuppressive substance of the present invention may be used together with a pharmaceutically acceptable compound having another activity, to prepare a pharmaceutical preparation.

The dose of the immunosuppressive substance of the present invention may be appropriately set or adjusted in accordance with an administration form, an administration route, a degree or stage of a target disease, and the like. For example, in the case of oral administration, a dose of the immunosuppressive substance may be set at 1–100 mg/kg body weight/day, preferably 1–10 mg/kg body weight/day. In the case of administration by injection, a dose of the immunosuppressive substance may be set at 1–50 mg/kg body weight/day, more preferably, 1–5 mg/kg body weight/day. In the case of percutaneous administration, a dose of the immunosuppressive substance may be set at 1–100 mg/kg body weight/day, more preferably, 1–10 mg/kg body weight/day. In the case of rectal administration, a dose of the immunosuppressive substance may be set at 1–50 mg/kg body weight/day, more preferably 1–5 mg/kg body weight/day. In the case of intraocular administration, about a 0.01–3% solution of the immunosuppressive substance may be applied dropwise to an eye several times per day. However, the doses are not limited to these.

EXAMPLES

The present invention will now be described by way of its Examples. However, the present invention is not limited to these Examples.

Synthesis Examples

The present invention will be described with reference to sulfofucosylstearoylglycerol derivative, which is one of the effective ingredients used in the immunosuppressive agent of the present invention, will be described hereinafter.

Example 1

Reaction a: 2,3,4,6-tetra-0-acetyl-α-D-galactopyranosyl bromide (ii)

2.4 mL of 60% perchloric acid was added dropwise to 400 mL of acetic anhydride at 0° C. After the temperature of the solution was raised to room temperature, 100 g of D-galactose (555 mmol) was added, with stirring, to the solution, while the temperature of the mixture was maintained in the range of 30 to 40° C. The reaction mixture was cooled to 20° C., and then 30.0 g of red phosphorus (969 mmol) was added to the reaction mixture. While the liquid temperature was maintained at 20° C. or lower, 180 g of bromine (2.25 mol) and then 36 mL of water were added dropwise to the reaction mixture. After being left for 2 hours at room temperature, 300 mL of cold chloroform was added to the reaction mixture. Thereafter, the reaction mixture was filtered with a glass filter. The filtrate was poured to 800 mL of cold water and the chloroform layer was separated by using a separatory funnel. The water layer was extracted with 50 mL of chloroform. The organic layer was combined with the previously separated chloroform layer and the resulting chloroform layer was washed with 300 mL of cold water. The chloroform layer was poured to 500 mL of a saturated solution of sodium hydrogencarbonate. The mixture was thoroughly agitated by using a separatory funnel, and the chloroform layer was collected. After being dried over anhydrous sodium sulfate, the chloroform layer was filtered, concentrated in vacuo and purified with silica gel flush chromatography (chloroform). The obtained crystalline substance was recrystallized with cold diisopropyl ether, whereby pure crystals were obtained.

Yield: 164 g (399 mmol), recovery: 71.9%, melting point: 75 to 81° C., $[\alpha]_D=+215°$ (c 1.78 $CHCl_3$)

$^1$H NMR (400 MHz, $CDCl_3$+TMS, δ); 6.70 (1H, d, J=3.9, H1), 5.52 (1H, dd, J=3.0 & 0.6, H4), 5.40 (1H, dd, J=10.6 & 3.3, H3), 5.05 (1H, dd, J=10.6 & 4.0, H2), 4.49 (1H, app t, J=6.5, H5), 4.19 (1H, dd, J=11.4 & 6.3, H6a), 4.11 (1H, dd, J=11.4 & 6.8, H6b), 2.16 (3H, s, Me), 2.12 (3H, s, Me), 2.07 (3H, s, Me), 2.02 (3H, s, Me)

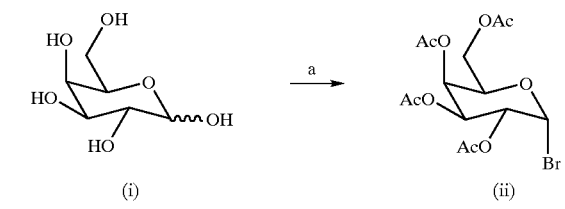

Reaction b: 2,3,4,6-tetra-0-acetyl-1-0-(2-propenyl)-β-D-galactose (iii)

170 g of the compound (ii) (413 mmol) was dissolved in 350 mL of dichloromethane and 60.0 mL of allyl alcohol (830 mol) was added thereto. Then, 104 g of mercury cyanide (412 mmol) was added to the solution and the reaction mixture was stirred overnight at room temperature. The reaction mixture was filtered with suction using Celite, washed with cold water and then washed with brine. After being dried over anhydrous sodium sulfate, the filtrate was again filtered, concentrated in vacuo and purified with silica gel flush chromatography (hexane:ethyl acetate=6:1→3:1). The obtained crystalline substance was recrystallized with cold diisopropyl ether, whereby pure crystals were obtained.

Yield: 151 g (389 mmol), recovery: 94.2%, melting point: 55 to 57° C., $[\alpha]_D=-15.4°$ (c 2.26 $CHCl_3$)

¹H NMR (400 MHz, CDCl₃+TMS, δ); 5.86 (1H, m, H2), 5.39 (1H, dd, J=3.4 & 1.0, H4'), 5.28 (1H, dq, J=17.3 & 1.6, H3a), 5.25 (1H, dd, J=10.5 & 7.9, H2'), 5.21 (1H, dq, J=10.5 & 1.6, H3b), 5.03 (1H, dd, J=10.5 & 3.4, H3'), 4.53 (1H, d, J=8.0, H1'), 4.36 (1H, ddt, J=13.2 & 4.9 & 1.4, H1a), 4.19 (1H, dd, J=11.2 & 6.6, H6'a), 4.13 (1H, dd, J=11.2 & 6.9, H6'b), 4.11 (1H, ddt, J=13.2 & 6.1 & 1.4, H1b), 3.91 (1H, dt, J=6.7 & 1.1, H5'), 2.16 (3H, s, Me), 2.06 (3H, s, Me), 2.05 (3H, s, Me), 1.99 (3H, s, Me)

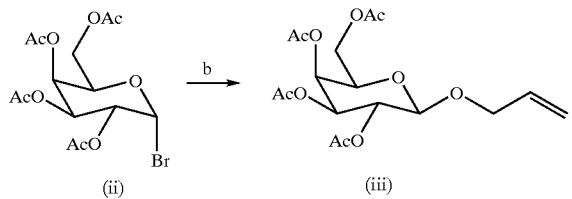

(ii)    (iii)

Reaction c: 1-0-(2-propenyl)-β-D-galactose (iv)

151 g of the compound (iii) (389 mmol) was dissolved in 300 mL of methanol, and 7.50 mL (38.9 mmol) of 28% sodium methoxide/methanol solution was added dropwise thereto, with stirring. The reaction mixture was stirred overnight at room temperature. The reaction mixture was then concentrated and purified with silica gel flush chromatography (chloroform:methanol=6:1→3:1), whereby colorless, needle crystals were obtained.

Yield: 77.2 g (351 mmol), recovery: 90.2%, melting point: 93 to 95° C., [α]$_D$=−1.21° (c 2.28 MeOH)

¹H NMR (400 MHz, CD₃OD, δ); 5.96 (1H, m, H2), 5.32 (1H, dq, J=17.2 & 1.6, H3a), 5.15 (1H, dq, J=10.4 & 1.6, H3b), 4.37 (1H, ddt, J=12.8 & 5.2 & 1.4, H1a), 4.26 (1H, d, J=7.2, H1'), 4.15 (1H, ddt, J=12.8 & 6.2 & 1.2, H1b), 3.83 (1H, app d, J=3.2, H4'), 3.75 (1H, dd, J=10.8 & 6.8, H6'a), 3.71 (1H, dd, J=10.8 & 5.6, H6'b), 3.54 (1H, dd, J=7.6 & 9.6, H2'), 3.49 (1H, app t, J=6.4, H5'), 3.47 (1H, dd, J=10.0 & 3.2, H3')

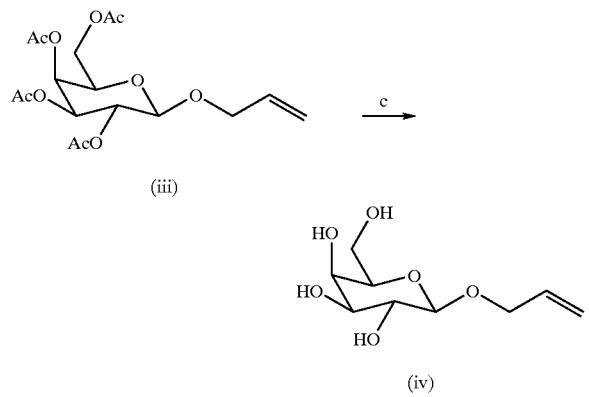

Reaction d: 1-0-(2-propenyl)-6-0-triphenylmethyl-β-D-galactose (v)

77.2 g of the compound (iv) (351 mmol) was dissolved in 300 mL of dry pyridine, and 117 g of trityl chloride (420 mmol) and 4.29 g of p-dimethylaminopyridine (DMAP) (35.1 mmol) were added thereto. The reaction mixture was stirred overnight at room temperature. The remaining trityl chloride was decomposed by adding approximately 10 mL of methanol to the reaction mixture. Thereafter, the reaction mixture was concentrated and cold water was added thereto. The mixture was then extracted with ethyl acetate. The organic layers were combined and neutralized with 1.0 N and 0.1 N hydrochloric acid to pH 4. The neutralized organic layer was washed with brine and dried over anhydrous sodium sulfate. Thereafter, the organic layer was filtered, concentrated in vacuo and purified with silica gel flush chromatography (dichloromethane:methanol=100:1→10:1), whereby colorless powdery crystals were obtained.

Yield: 160 g (346 mmol), recovery: 98.6%, melting point: 75 to 78° C., [α]$_D$=−2.51° (c 2.82 CHCl₃)

¹H NMR (400 MHz, CD₃OD, δ); 7.47–7.44 (6H, m, Ar), 7.29–7.19 (9H, m, Ar), 5.99 (1H, m, H2), 5.33 (1H, dq, J=17.4 & 1.6, H3a), 5.16 (1H, dq, J=10.4 & 1.6, H3b), 4.38 (1H, ddt, J=12.8 & 5.2 & 1.6, H1a), 4.27 (1H, d, J=7.6, H1'), 4.20 (1H, ddt, J=12.8 & 6.0 & 1.2, H1b), 3.77 (1H, dd, J=3.4 & 1.0, H4'), 3.56 (1H, ddd, J=7.2 & 4.8 & 1.0, H5'), 3.52 (1H, dd, J=7.6 & 9.6, H2'), 3.45 (1H, dd, J=9.6 & 7.2, H6'a), 3.44 (1H, dd, J=9.6 & 3.2, H3'), 3.24 (1H, (dd, J=9.6 & 4.8, H6'b)

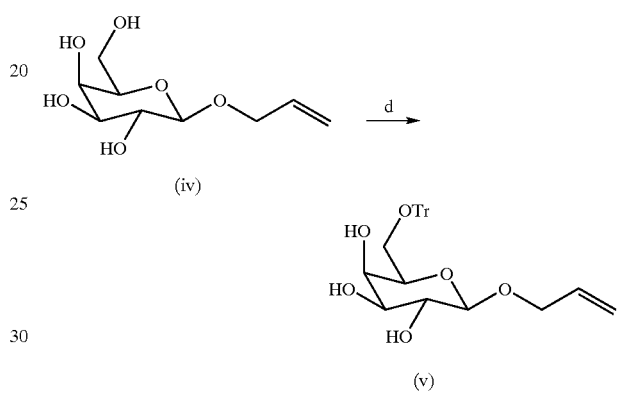

Reaction e: 2,3,4-tri-0-benzyl-1-0-(2-propenyl)-β-D-galactose (vi)

22.4 g of 80% sodium hydride (748 mmol) which had been dispersed in mineral oil was put in a reaction vessel and thoroughly washed with dry hexane. Hexane was then removed therefrom and 69.1 g of the compound (v) (149 mmol) which had been dissolved in dry N,N-dimethylformamide (DMF) was added dropwise thereto, while the mixture was cooled with ice. After 15 minutes, the temperature of the reaction mixture was raised to room temperature. The reaction mixture was then stirred for 1 hour. Next, 102 g of benzyl bromide (598 mmol) was added dropwise to the reaction mixture, while the reaction mixture was again cooled with ice. After 15 minutes, the temperature of the reaction mixture was raised to room temperature. The reaction mixture was then stirred for 3 hours. Thereafter, excessive sodium hydride was decomposed with methanol. Cold water was added to the reaction mixture. The mixture was then extracted with ethyl acetate. The organic layers were combined, washed with brine and dried over anhydrous sodium sulfate. Thereafter, the organic layer was filtered, subjected to concentration in vacuo, whereby an oily substance was obtained (Reaction e-1).

Next, the oily substance was dissolved in toluene:methanol=1:1 and 9.99 g of p-toluenesulfonic acid. monohydrate (52.5 mmol) was added thereto. The reaction mixture was stirred overnight at room temperature. Thereafter, the reaction was quenched by adding cold water. The mixture was then extracted with ethyl acetate. The organic layers were combined, washed with brine and dried over anhydrous sodium sulfate. Thereafter, the organic layer was filtered, concentrated in vacuo and purified with silica gel flush chromatography (hexane:ethyl acetate=6:1→3:1), whereby colorless, needle crystals were obtained (Reaction e-2).

Yield: 49.5 g (101 mmol), recovery: 71.9%, melting point: 74 to 75° C., $[\alpha]_D=-2.82°$ (c 2.45 CHCl$_3$)

$^1$H NMR (400 MHz, CDCl$_3$+TMS, δ); 7.37–7.27 (15H, m, Ar), 5.94 (1H, m, H2), 5.31 (1H, dq, J=17.2 & 1.6, H3a), 5.17 (1H, dq, J=10.4 & 1.6, H3b), 4.95 (1H, d, J=11.8, Ar—CH$_2$), 4.94 (1H, d, J=10.8, Ar—CH$_2$), 4.80 (1H, d, J=11.6, Ar—CH$_2$), 4.77 (1H, d, J=10.8, Ar—CH$_2$), 4.73 (1H, d, J=11.6, Ar—CH$_2$), 4.65 (1H, d, J=11.8, Ar—CH$_2$), 4.41 (1H, d, J=7.6, H1'), 4.40 (1H, ddt, J=12.8 & 5.2 & 1.6, H1a), 4.13 (1H, ddt, J=12.8 & 6.0 & 1.6, H1b), 3.86 (1H, dd, J=9.6 & 7.6, H2'), 3.77 (1H, app d, J=2.4, H4'), 3.76 (1H, dd, J=11.2 & 7.2, H6'a), 3.44 (1H, dd, J=9.6 & 2.8, H3'), 3.49 (1H, dd, J=11.2 & 5.6, H6'b), 3.36 (1H, app t, J=6.2, H5')

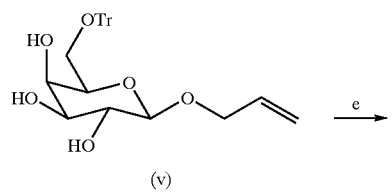

(v)

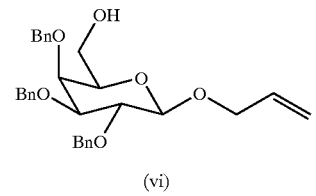

(vi)

Reaction f: 2,3,4-tri-0-benzyl-1-0-(2-propenyl)-6-0-(4-tolylsulfonyl)-β-D-galactose (vii)

21.6 g of the compound (vi) (44.0 mmol) was dissolved in 200 mL of dry pyridine, and 538 mg of DMAP (4.40 mmol) and 12.6 g of p-toluenesulfonyl chloride (66.1 mmol) were added thereto. The reaction mixture was stirred overnight at room temperature. The reaction was quenched by adding cold water to the reaction mixture. The reaction mixture was then extracted with ethyl acetate. The organic layers were combined and neutralized with 1.0 N and 0.1 N hydrochloric acid to pH 4. The neutralized organic layer was washed with brine and dried over anhydrous sodium sulfate. Thereafter, the organic layer was filtered, concentrated in vacuo and purified with silica gel flush chromatography (hexane:ethyl acetate=6:1→3:1), whereby an oily substance was obtained.

Yield: 27.5 g (42.6 mmol), recovery: 96.8%, $[\alpha]_D=+3.08°$ (c 1.17 CHCl$_3$)

$^1$H NMR (400 MHz, CDCl$_3$+TMS, δ); 7.37–7.27 (2H, d, J=8.3, H at the side of Ts-SO$_2$), 7.37–7.26 (15H, m, Ar), 7.20–7.18 (2H, m, H at the side of Ts-CH$_3$), 5.90 (1H, m, H2), 5.30 (1H, dq, J=17.2 & 1.5, H3a), 5.17 (1H, dq, J=10.4 & 1.3, H3b), 4.91 (1H, d, J=11.4, Ar—CH$_2$), 4.90 (1H, d, J=10.8, Ar—CH$_2$), 4.78 (1H, d, J=11.8, Ar—CH$_2$), 4.73 (1H, d, J=10.8, Ar—CH$_2$), 4.71 (1H, d, J=11.8, Ar—CH$_2$), 4.48 (1H, d, J=11.4, Ar—CH$_2$), 4.36 (1H, d, J=7.7, H1'), 4.32 (1H, ddt, J=13.0 & 5.1 & 1.4, H1a), 4.08 (1H, dd, J=10.0 & 6.4, H6'a), 4.05 (1H, ddt, J=13.0 & 6.0 & 1.2, H1b), 3.95 (1H, dd, J=10.3 & 6.0, H6'b), 3.79 (1H, app d, J=2.4, H4'), 3.79 (1H, dd, J=9.6 & 7.8, H2'), 3.59 (1H, app t, J=6.4, H5'), 3.49 (1H, Hdd, J=9.7 & 2.9, H3'), 2.42 (3H, s, Me)

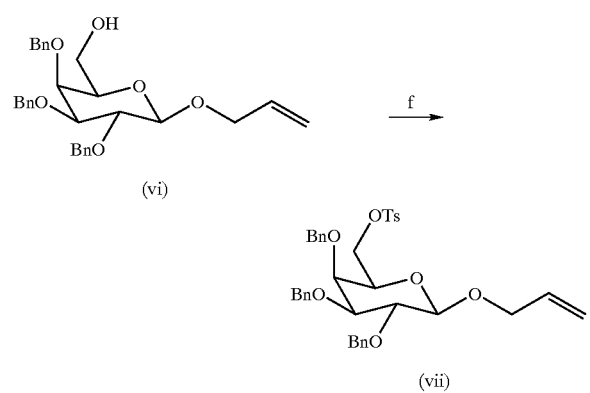

(vi)

(vii)

Reaction g: 2,3,4-tri-0-benzyl-1-0-(2-propenyl)-6-deoxy-6-acetylthio-β-D-galactose (viii)

27.5 g of the compound (vii) (42.6 mmol) was dissolved in 200 mL of dry DMF, and 7.32 g of potassium thioacetate (64.1 mmol) was added thereto. The reaction mixture was stirred overnight at 80° C. The reaction was quenched by adding cold water to the reaction mixture. The mixture was then extracted with ethyl acetate. The extraction was washed with brine and dried over anhydrous sodium sulfate. Thereafter, the obtained crystals were recrystallized with ethanol, whereby a white crystalline substance was obtained.

Yield: 16.4 g (29.9 mmol), recovery: 70.2%, melting point: 74 to 76° C., $[\alpha]_D=-2.84°$ (c 2.48 CHCl$_3$)

$^1$H NMR (400 MHz, CDCl$_3$+TMS, δ); 7.37–7.25 (15H, m, Ar), 5.95 (1H, m, H2), 5.33 (1H, dq, J=17.4 & 1.6, H3a), 5.19 (1H, dq, J=10.4 & 1.6, H3b), 5.01 (1H, d, J=11.6, Ar—CH$_2$), 4.94 (1H, d, J=11.2, Ar—CH$_2$), 4.80 (1H, d, J=11.8, Ar—CH$_2$), 4.75 (1H, d, J=11.2, Ar—CH$_2$), 4.74 (1H, d, J=11.8, Ar—CH$_2$), 4.65 (1H, d, J=11.6, Ar—CH$_2$), 4.42 (1H, ddt, J=13.2 & 5.2 & 1.6, H1a), 4.36 (1H, d, J=7.6, H1'), 4.13 (1H, ddt, J=13.2 & 6.0 & 1.6, H1b), 3.82 (1H, dd, J=9.6 & 7.6, H2'), 3.81 (1H, app d, J=2.8, H4'), 3.50 (1H, dd, J=9.6 & 2.9, H3'), 3.33 (1H, app t, J=6.8, H5'), 3.13 (1H, dd, J=13.8 & 7.8, H6'a), 3.01 (1H, dd, J=13.8 & 5.6, H6'b), 2.31 (3H, s, Me)

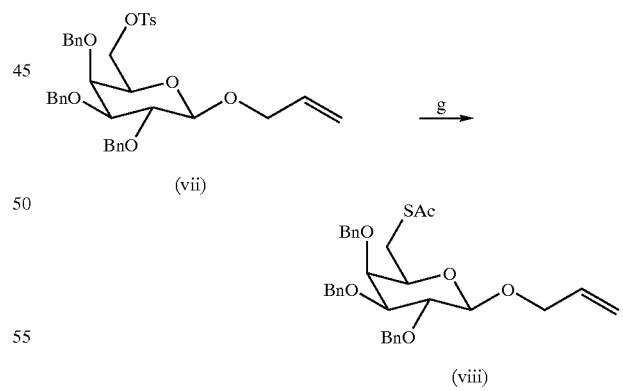

(vii)

(viii)

Reaction h: 3-0-(2,3,4-tri-0-benzyl-6-deoxy-6-acetylthio-β-D-galactopyranosyl)-glycerol (ix)

6.50 g of the compound (viii) (11.8 mmol) was dissolved in 150 mL of a solution (t-butyl alcohol:water=4:1). 2.90 g of trimethylamine N-oxide.dihydrate (26.1 mmol). and 15.0 mL of 0.04 M osmium tetraoxide/t-butyl alcohol solution were added to the solution of the compound (viii). The reaction mixture was stirred over two nights at room temperature. Thereafter, activated charcoal was added to the reaction mixture, and the mixture was stirred for 1.5 hours at room temperature. The reaction mixture was then filtered with suction using Celite. Cold water was added to the filtrate. The mixture was then extracted with ethyl acetate. The organic layers were combined, washed with brine, dried over anhydrous sodium sulfate, filtered and concentrated in vacuo. The obtained crystals were recrystallized with chloroform and hexane, whereby a white crystalline substance was obtained.

Yield: 4.73 g (8.12 mmol), recovery: 68.8%, melting point: 108 to 110° C., $[\alpha]_D=+8.02°$ (c 1.74 CHCl$_3$)

$^1$H NMR (400 MHz, CDCl$_3$+TMS, δ); 7.37–7.25 (15H, m, Ar), 5.03–4.63 (6H, m, Ar—CH$_2$), 4.33 (1H, m, H1'), 3.90–3.50 (9H, m, H1a, b & H2 & H3a, b & H2' & H3' & H4'), 3.37 (1H, m, H5'), 3.10 (1H, m, H6'a), 2.98 (1H, m6, H6'b), 2.31 (3H, app s, Me)

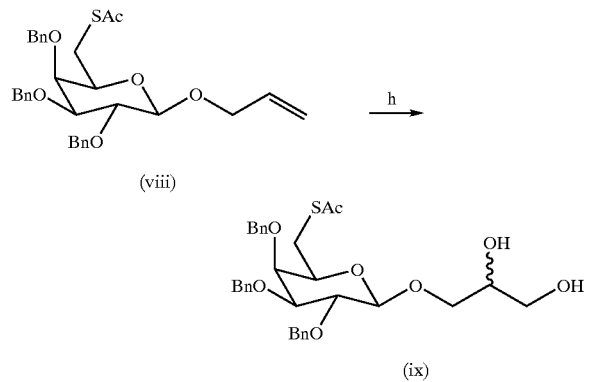

(viii)

(ix)

Reaction i: 3-0-(2,3,4-tri-0-benzyl-6-deoxy-6-acetylthio-β-D-galactopyranosyl)-1,2-di-0-stearoyl-glycerol (x-1)

3-0-(2,3,4-tri-0-benzyl-6-deoxy-6-acetylthio-β-D-galactopyranosyl)-1-0-stearoyl-glycerol (x-2)

1.00 g of the compound (ix) (1.72 mmol) was dissolved in 50 mL of dry dichloromethane, and 560 mg of 1-ethyl-3-(3-dimethylaminopropyl)-carbodiimide hydrochloride (EDCl) (2.92 mmol), 336 mg of DMAP (2.75 mmol) and 733 mg of stearic acid (2.58 mmol) were added to the solution of the compound (ix). The reaction mixture was stirred for 5 hours at room temperature. 50 mL of dichloromethane was added to the reaction mixture. The mixture was then washed with brine, dried over anhydrous sodium sulfate, filtered, concentrated in vacuo and purified with silica gel flush chromatography (hexane:ethyl acetate= 7:1→3:1), thereby diester and monoester were eluted in this order. As a result, diester (yield: 798 mg, i.e., 715 μmol) and monoester (yield: 784 mg, i.e., 923 μmol) as white, non-crystalline solid substances were obtained (recovery: 95.2%).

Diester (x-1): melting point 49 to 53° C.; $[\alpha]_D=+2.70°$ (c 1.63 CHCl$_3$)

$^1$H NMR (400 MHz, CDCl$_3$+TMS, δ); 7.37–7.25 (15H, m, Ar), 5.26 (1H, m, H2), 5.02–4.62 (6H, m, Ar—CH$_2$), 4.42–4.11 (3H, m, H1a, b & H1'), 4.07–4.01 (1H, m, H3a), 3.80–3.76 (2H, m, H2' & H4'), 3.70–3.63 (1H, m, H3b), 3.49 (1H, app dd, J=9.7 & 2.6, H3'), 3.32 (1H, app t, J=6.0, H5'), 3.14–3.05 (1H, m, H6'a), 3.00–2.94 (1H, m, H6'b), 2.31–2.22 (7H, m, SAc & COCH$_2$), 1.60–1.57 (4H, m, COCH$_2$CH$_2$), 1.25 (56H, br, —CH$_2$—), 0.88 (6H, br t, J=6.6, Me)

Monoester (x-2): melting point 46 to 49° C.; $[\alpha]_D=+4.12°$ (c 1.69 CHCl$_3$)

$^1$H NMR (400 MHz, CDCl$_3$+TMS, δ) 7.35–7.25 (15H, m, Ar), 5.03–4.63 (6H, m, Ar—CH$_2$), 4.32 (1H, br d, J=7.7, H1'), 4.19–3.69 (7H, m, H1a, b & H2 & H3a, b & H2' & H4'), 3.52 (1H, app dd, J=9.7 & 2.6, H3'), 3.37 (1H, app t, J=6.4, H5'), 3.13–3.07 (1H, m, H6'a), 3.01–2.91 (1H, m, H6'b), 2.35–2.27 (5H, m, SAc & COCH$_2$), 1.64–1.59 (2H, m, COCH$_2$CH$_2$), 1.25 (28H, br, —CH$_2$—), 0.88 (3H, br t, J=6.6, Me)

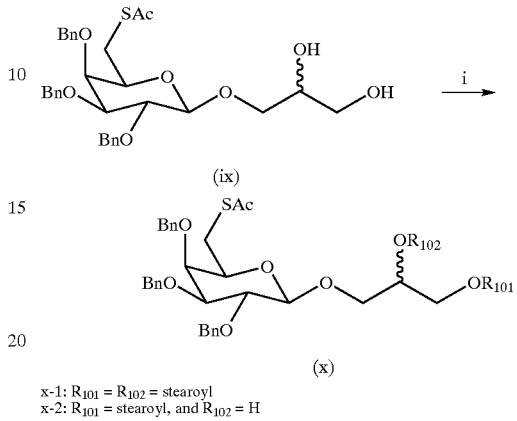

(ix)

(x)

x-1: R$_{101}$ = R$_{102}$ = stearoyl
x-2: R$_{101}$ = stearoyl, and R$_{102}$ = H Reaction j-1: 3-0-(2,3,4-tri-0-benzyl-6-deoxy-6-sulfo-β-D-galactopyranosyl)-1,2-di-0-stearoyl-glycerol sodium salt (xi-1)

500 mg of the compound (x-1) (448 μmol) was dissolved in 20 mL of acetic acid, and 500 mg of potassium acetate and 826 mg of OXONE (2KHSO$_5$, KHSO$_4$, K$_2$SO$_4$) were added thereto. The reaction mixture was stirred overnight at room temperature. Thereafter, cold water was added to the reaction mixture, to quench the reaction. The reaction mixture was then extracted with ethyl acetate. The organic layers were combined and neutralized with a solution of sodium hydroxide and a saturated solution of sodium carbonate. The neutralized extraction was then washed with brine, dried over anhydrous sodium sulfate, filtered, concentrated in vacuo and purified with silica gel flush chromatography (chloroform:methanol=100:0→10:1), whereby a white, non-crystalline solid substance was obtained.

Yield: 452 mg (395 μmol), recovery: 88.2%, melting point: 49 to 53° C., $[\alpha]_D=+2.70°$ (c 1.63 CHCl$_3$)

$^1$H NMR (400 MHz, CDCl$_3$+TMS, δ); 7.23 (15H, br, Ar), 5.27 (1H, br, H2), 4.84–3.30 (17H, br m, Ar—CH$_2$ & H1a, b & H3a, b & H1' & H2' & H3' & H4' & H5' H6'a, b), 2.14 (4H, br, COCH$_2$), 1.46 (4H, br, COCH$_2$CH$_2$), 1.25 (56H, br, —CH$_2$—), 0.88 (6H, br t, J=6.2, Me)

Reaction j-2: 3-0-(2,3,4-tri-0-benzyl-6-deoxy-6-sulfo-β-D-galactopyranosyl)-1-0-stearoyl-glycerol sodium salt (xi-2)

500 mg of the compound (x-2) (589 μmol) was dissolved in 20 mL of acetic acid, and 500 mg of potassium acetate and 1.09 g of OXONE (1.77 mmol) were added thereto. The reaction mixture was stirred overnight at room temperature. Thereafter, cold water was added to the reaction mixture, to quench the reaction. The reaction mixture was then extracted with ethyl acetate. The organic layers were combined and neutralized with a solution of sodium hydroxide and a saturated solution of sodium carbonate. The neutralized extraction was then washed with brine, dried over anhydrous sodium sulfate, filtered, concentrated in vacuo and purified with silica gel flush chromatography (chloroform:methanol= 100:0→10:1), whereby a white, non-crystalline solid substance was obtained.

Yield: 187 mg (207 μmol), recovery: 35.1%, melting point: 46 to 49° C., $[\alpha]_D=+4.12°$ (c 1.69 CHCl$_3$)

$^1$H NMR (400 MHz, CDCl$_3$+TMS, δ); 7.23 (15H, br, Ar), 4.82–3.30 (18H, br m, Ar—CH$_2$ & H1a, b & H2 & H3a, b

& H1' & H2' & H3' & H4' & H5' H6'a, b), 2.11 (2H, br, COCH$_2$), 1.44 (2H, br, COCH$_2$CH$_2$), 1.25 (28H, br, —CH$_2$—), 0.88 (3H, br t, J=6.2, Me)

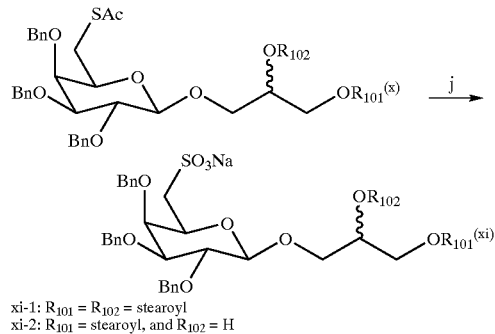

xi-1: R$_{101}$ = R$_{102}$ = stearoyl
xi-2: R$_{101}$ = stearoyl, and R$_{102}$ = H Reaction k-1: 3-0-(6-deoxy-6-sulfo-β-D-galactopyranosyl)-1,2-di-0-stearoyl-glycerol sodium salt (xii-1)

452 mg of the compound (xi-1) (395 μmol) was dissolved in 50 mL of ethanol in a flask, and 1.00 g of 10% palladium-activated charcoal (Pd—C) was added thereto. The atmosphere in the flask was substituted with hydrogen gas. In this state, the reaction mixture was stirred overnight at room temperature. Thereafter, the reaction mixture was filtered with suction using Celite, concentrated in vacuo, and purified with silica gel flush chromatography (chloroform:methanol=10:1→chloroform:methanol:water= 65:25:4), whereby a white, non-crystalline solid substance was obtained.

Yield: 210 mg (240 μmol), recovery: 53.8%, melting point and specific rotation have not been measured.

$^1$H NMR (400 MHz, CDCl$_3$+CD$_3$OD+D$_2$O+TMS, δ); 5.27 (1H, m, H2), 4.45–4.10 (4H, m, H1a, b & H1' & H3a), 4.02–3.94 (2H, m, H2' & H4'), 3.74–3.68 (1H, m, H3b), 3.64–3.61 (1H, m, H3'), 3.55–3.49 (1H, m, H5'), 3.45–3.38 (1H, m, H6'a), 3.18–3.14 (1H, m, H6'b), 2.36–2.29 (4H, m, COCH$_2$), 1.60 (4H, br, COCH$_2$CH$_2$), 1.25 (56H, br, —CH$_2$—), 0.89 (6H, br t, J=6.6, Me)

Reaction k-2: 3-0-(6-deoxy-6-sulfo-β-D-galactopyranosyl)-1-0-stearoyl-glycerol sodium salt (xii-2)

187 mg of the compound (xi-2) (213 μmol) was dissolved in 30 mL of ethanol in a flask, and 500 mg of 10% Pd—C was added thereto. The atmosphere in the flask was substituted with hydrogen gas, and the reaction mixture was stirred overnight at room temperature. Thereafter, the reaction mixture was filtered with suction using Celite, concentrated in vacuo, and purified with silica gel flush chromatography (chloroform:methanol= 10:1→chloroform:methanol:water=65:25:4), whereby a white, non-crystalline solid substance was obtained.

Yield: 32.0 mg (52.7 μmol), recovery: 24.7%, melting point and specific rotation have not been measured.

$^1$H NMR (400 MHz, CDCl$_3$+CD$_3$OD+D$_2$O+TMS, δ); 4.30–3.54 (10H, m, H1a, b & H2 & H3a, b & H1' & H2' & H3' & H4' & H5'), 3.30–3.15 (1H, m, H6'a, b), 2.36–2.29 (2H, br t, J=7.6, COCH$_2$), 1.60 (2H, br t, J=7.1, COCH$_2$CH$_2$), 1.30 (28H, br, —CH$_2$—), 0.89 (3H, br t, J=6.7, Me)

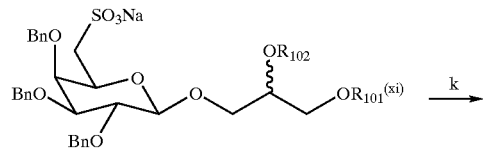

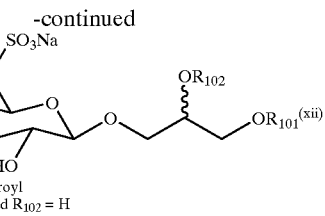

xii-1: R$_{101}$ = R$_{102}$ = stearoyl
xii-2: R$_{101}$ = stearoyl, and R$_{102}$ = H <Assay 1>
Mixed Lymphocytes Reaction Lymphocytes serving as stimulator cells and responder cells were prepared from blood taken from individual healthy persons.

The responder cells were further separated from the lymphocyte cells to give T lymphocytes alone.

No treatment was applied to the responder cells. $10^6$/mL of the stimulator cells were treated with 10 μg/mL of mitomycin C to stop the cell growth.

Subsequently, the responder cells were inoculated in a 96-well plate, at a rate of $10^5$ cells per well, and then test substances (compound Nos. 1 to 12 listed in Table 1 below) were added to a predetermined concentration. The reaction mixture was cultured at 37° C. for one hour. Thereafter, the stimulator cells were added at a rate of $10^5$ cells per well. The mixture was cultured in a CO$_2$ incubator at 37° C. for 4 days. After the incubation, the proliferation ability of the responder cells was quantified as follows. First, [$^3$H]-thymidine was added to the responder cells and incorporated into the nucleus of the cells by culturing the cells for 16 hours. Then, the amount of [$^3$H]-thymidine uptake into the cells was determined by a scintillation counter.

TABLE 1

(1)

| Compound | R$_{101}$— | R$_{102}$— |
|---|---|---|
| 1) α-SFMG14:0 | CH$_3$(CH$_2$)$_{12}$CO— | H |
| 2) α-SFMG16:0 | CH$_3$(CH$_2$)$_{14}$CO— | H |
| 3) α-SFMG18:0 | CH$_3$(CH$_2$)$_{16}$CO— | H |
| 4) α-SFDG14:0 | CH$_3$(CH$_2$)$_{12}$CO— | CH$_3$(CH$_2$)$_{12}$CO— |
| 5) α-SFDG16:0 | CH$_3$(CH$_2$)$_{14}$CO— | CH$_3$(CH$_2$)$_{14}$CO— |
| 6) α-SFDG18:0 | CH$_3$(CH$_2$)$_{16}$CO— | CH$_3$(CH$_2$)$_{16}$CO— |
| 7) β-SFMG14:0 | CH$_3$(CH$_2$)$_{12}$CO— | H |
| 8) β-SFMG16:0 | CH$_3$(CH$_2$)$_{14}$CO— | H |
| 9) β-SFMG18:0 | CH$_3$(CH$_2$)$_{16}$CO— | H |
| 10) β-SFDG14:0 | CH$_3$(CH$_2$)$_{12}$CO— | CH$_3$(CH$_2$)$_{12}$CO— |
| 11) β-SFDG16:0 | CH$_3$(CH$_2$)$_{14}$CO— | CH$_3$(CH$_2$)$_{14}$CO— |
| 12) β-SFDG18:0 | CH$_3$(CH$_2$)$_{16}$CO— | CH$_3$(CH$_2$)$_{16}$CO— |

Figure 2:
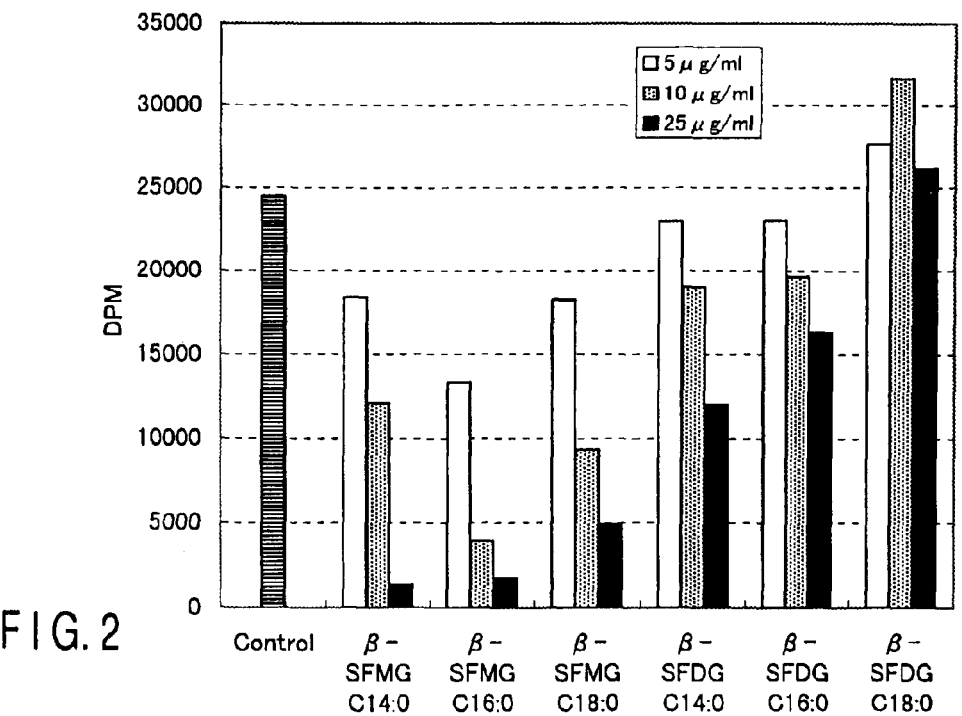
FIG. 2 is a graph showing immunosuppressive activity of the compound represented by the general formula (1) of the present invention.

The results are shown in FIGS. 1 and 2. In each of the FIGS. 1 and 2, the vertical axis indicates the intensity of radioactivity.

FIG. 1 shows the amounts of [$^3$H]-thymidine uptake when compound Nos. 1 to 6 of various concentrations (2.5 μg/mL, 5 μg/mL, 10 μg/mL, and 25 μg/mL) are added. FIG. 1 also shows the amounts of [$^3$H]-thymidine uptake of a control sample. The lower the amount of [$^3$H]-thymidine uptake, the higher the immunosuppressive activity.

FIG. 2 shows the amounts of [$^3$H]-thymidine uptake when compound Nos. 7 to 12 of various concentrations (5 μg/mL, 10 μg/mL, and 25 μg/mL) are added. FIG. 2 also shows the amounts of [$^3$H]-thymidine uptake of a control sample. The lower the amount of [$^3$H]-thymidine uptake, the higher the immunosuppressive activity.

As is apparent from FIGS. 1 and 2, all test substances have significant immunosuppressive activities. In particular, the immunosuppressive activity of sulfofucosylmonoacylglycerols, which are represented by the general formula (1) wherein $R_{102}$ is a hydrogen atom, tended to be higher than that of sulfofucosyldiacylglycerols. Note that significant immunosuppressive activity of compound No. 12 (β-SFDG 18:0) was not confirmed in this assay.

Among the commercially available immunosuppressive agents, a small number thereof (e.g. FK506 or the like) is known to exhibit a rejection symptoms-suppression effect in dermal graft experiments. However, there has been known no immunosuppressive agent having a high rejection symptoms-suppression effect and low toxicity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for immunosuppression in a subject comprising administering to the subject in need thereof, an immunosuppressively effective amount of at least one sulfofucosylacylglycerol compound represented by formula (1):

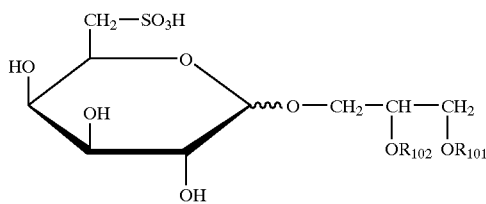

(1)

wherein $R_{101}$ represents an acyl residue of a higher fatty acid, and $R_{102}$ represents a hydrogen atom or acyl residue of a higher fatty acid; or a pharmaceutically acceptable salt thereof.

2. The method according to claim 1, wherein $R_{101}$ is an acyl residue represented by R—C(=O)—, wherein R represents an alkyl or alkenyl group having 13–25 carbon atoms, and $R_{102}$ is a hydrogen atom or acyl residue represented by R'—C(=O)—, wherein R' represents an alkyl or alkenyl group having 13–25 carbon atoms.

3. The method according to claim 1, wherein $R_{101}$ is an acyl residue of a higher fatty acid, and $R_{102}$ represents a hydrogen atom.

4. The method according to claim 3, wherein $R_{101}$ is an acyl residue represented by R—C(=O)—, wherein R represents an alkyl or alkenyl group having 13–25 carbon atoms.

5. The method according to claim 1, wherein each of $R_{101}$ and $R_{102}$ independently represents an acyl residue of a higher fatty acid.

6. The method according to claim 5, wherein each of $R_{101}$ and $R_{102}$ independently is an acyl residue represented by R—C(=O)—, wherein R represents an alkyl or alkenyl group having 13–25 carbon atoms.

7. The method according to claim 1, wherein the sulfofucosylacylglycerol compound is represented by formula (2):

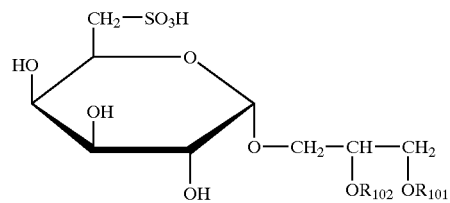

(2)

wherein $R_{101}$ represents an acyl residue of a higher fatty acid, and $R_{102}$ represents a hydrogen atom or acyl residue of a higher fatty acid.

8. The method according to claim 7, wherein $R_{101}$ is an acyl residue represented by R—C(=O)—, wherein R represents an alkyl or alkenyl group having 13–25 carbon atoms, and $R_{102}$ is a hydrogen atom or acyl residue represented by R'—C(=O)—, wherein R' represents an alkyl or alkenyl group having 13–25 carbon atoms.

9. The method according to claim 7, wherein $R_{101}$ is an acyl residue of a higher fatty acid, and $R_{102}$ represents a hydrogen atom.

10. The method according to claim 9, wherein $R_{101}$ is an acyl residue represented by R—C(=O)—, wherein R represents an alkyl or alkenyl group having 13–25 carbon atoms.

11. The method according to claim 7, wherein each of $R_{101}$ and $R_{102}$ independently represents an acyl residue of a higher fatty acid.

12. The method according to claim 11, wherein each of $R_{101}$ and $R_{102}$ independently is an acyl residue represented by R—C(=O)—, wherein R represents an alkyl or alkenyl group having 13–25 carbon atoms.

13. The method according to claim 1, wherein the sulfofucosylacylglycerol compound is represented by formula (3):

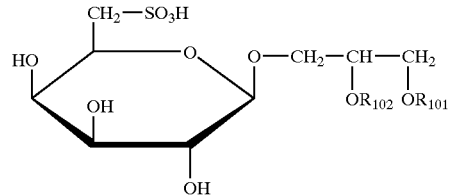

(3)

wherein $R_{101}$ represents an acyl residue of a higher fatty acid, and $R_{102}$ represents a hydrogen atom or acyl residue of a higher fatty acid.

14. The method according to claim 13, wherein $R_{101}$ is an acyl residue represented by R—C(=O)—, wherein R represents an alkyl or alkenyl group having 13–25 carbon atoms, and $R_{102}$ is a hydrogen atom or acyl residue represented by R'—C(=O)—, wherein R' represents an alkyl or alkenyl group having 13–25 carbon atoms.

15. The method according to claim 13, wherein $R_{101}$ is an acyl residue of a higher fatty acid, and $R_{102}$ represents a hydrogen atom.

16. The method according to claim 15, wherein $R_{101}$ is an acyl residue represented by R—C(=O)—, wherein R represents an alkyl or alkenyl group having 13–25 carbon atoms.

17. The method according to claim 13, wherein each of $R_{101}$ and $R_{102}$ independently represents an acyl residue of a higher fatty acid.

18. The method according to claim 17, wherein each of $R_{101}$ and $R_{102}$ independently is an acyl residue represented by R—C(=O)—, wherein R represents an alkyl or alkenyl group having 13–25 carbon atoms.

* * * * *